(12) United States Patent
Kumar et al.

(10) Patent No.: US 6,958,224 B2
(45) Date of Patent: Oct. 25, 2005

(54) CHIMERIC PROTEIN α BNAC CRYSTALLIN WITH EXTRAORDINARILY HIGH CHAPERONE-LIKE ACTIVITY AND A METHOD RELATED TO THE USE THEREOF

(75) Inventors: L. V. Siva Kumar, Hyderabad (IN); Chandra Mohan Rao, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 354 days.

(21) Appl. No.: 10/105,427

(22) Filed: Mar. 26, 2002

(65) Prior Publication Data

US 2002/0177192 A1 Nov. 28, 2002

Related U.S. Application Data

(60) Provisional application No. 60/279,223, filed on Mar. 28, 2001.

(51) Int. Cl.$^7$ .......................... A61K 38/17; C21P 21/02; C12N 5/06; C07K 14/435
(52) U.S. Cl. .................. 435/69.1; 435/320.1; 435/325; 530/350; 536/23.5; 514/12
(58) Field of Search ........................ 530/350; 435/69.1, 435/320.1, 325; 536/23.5; 514/12

*Primary Examiner*—Karen Cochrane Carlson
*Assistant Examiner*—Marsha Tsay
(74) *Attorney, Agent, or Firm*—Butzel Lorg

(57) ABSTRACT

The present invention relates to a chimera α BNAC of SEQ ID No.1 and a corresponding chimeric protein α BNAC crystallin of SEQ ID No. 2, with said chimeric protein having extraordinarily high chaperone-like activity and a method of preventing protein aggregation using said chimeric protein.

12 Claims, 10 Drawing Sheets

FIG. 1. Schematic description of the design of chimeric constructs.

AlphaBNAC

DNA Sequence:(DNA Sequence No.1)

```
atggacatcg ccatccacca cccctggatc cgccgcccct tctttccttt
ccactccccc agccgcctct ttgaccagtt cttcggagag cacctgttgg
agtctgatct tttcccgacg tctacttccc tgagtccctt ctaccttcgg
ccaccctcct tcctgcgggc acccagctgg tttgacactg gactctcaga
gatgcgcctg gagaaggaca ggtctctgt caacctggat gtgaagcacttctcc
ccggaggacc tcaccgtgaa ggtgcaggac gactttgtgg agatccacgg
aaagcacaac gagcgccagg acgaccacgg ctacatttcc cgtgagttcc
accgccgcta ccgcctgccg tccaacgtgg accagtcggc cctctcttgc
tccctgtctg ccgatggcat gctgaccttc tgtggcccca agatccagac
tggcctggat gccacccacg ccgagcgagc catccccgtg tcgcgggagg
agaagcccac ctcggctccc tcgtcc
```

Fig.9

Protein Sequence: (DNA Sequence No.2)

```
MDIAIHHPWI RRPFFPFHSP SRLFDQFFGE HLLESDLFPT STSLSPFYLR
PPSFLRAPSW FDTGLSEMRL EKDRFSVNLD VK*HF SPEDLTVKVQ DDFVEIHGKH
NERQDDHGYI SREFHRRYRL PSNVDQSALS CSLSADGMLT FCGPKIQTGL
DATHAERAIP VSREEKPTSA PSS
```

Fig.10

CHIMERIC PROTEIN α BNAC CRYSTALLIN WITH EXTRAORDINARILY HIGH CHAPERONE-LIKE ACTIVITY AND A METHOD RELATED TO THE USE THEREOF

Priority is hereby claimed to United States Provisional Patent Application Ser. No. 60/279,223, filed Mar. 28, 2001.

FIELD OF THE PRESENT INVENTION

The present invention relates to a chimera α BNAC of SEQ ID NO:1 and a corresponding chimeric protein α BNAC crystallin of SEQ ID NO:2, with the chimeric protein having extraordinarily high chaperone-like activity. The present invention further relates to a method of preventing protein aggregation using the described chimeric protein.

BACKGROUND OF THE PRESENT INVENTION

α-Crystallin, a major lens protein having homology with small heat shock proteins, prevents aggregation of other proteins like a molecular chaperone. The inventors had earlier shown that α-crystallin can prevent photo-aggregation of γ-crystallin, which may have relevance in cataractogenesis.

By using various non-thermal modes of aggregation, it was shown that chaperone-like activity of α-crystallin is temperature-dependent. A structural perturbation above 30° C. enhances this activity severalfold.

In order to probe the molecular mechanism of the chaperone-like activity and its enhancement upon structural perturbation, the inventors have studied α-crystallin and its constituent subunits The recent study of the αA and αB heteroaggregates showed that, despite high sequence homology, these proteins differ in their stability, chaperone-like activity, and the temperature dapendence of this activity. This study also indicated different roles for the two proteins in that α-crystallin heteroaggregate in the eye lens and as separate proteins in non-lenticular tissues.

Several investigators have introduced mutations in αA and αB crystallins to gain an insight into the structure-function relation. Derham and Harding in their recent review list about 30 site-directed mutations from different laboratories. These mutations either result in some decrease or no change in protective ability. It is interesting to note that point mutations in both αA and αB crystallin, R116C and R120G, respectively, result in significant loss of activity and are associated with human diseases.

Human αA and αB crystallins are coded by three exons and are thought to have arisen due to gene duplication. They share high sequence homology with the small heat shock proteins, which are found in all organisms, from prokaryotes to humans. αA and αB crystallins are constitutively expressed during normal growth and development. αA crystallin is expressed predominantly in the eye lens with small amounts being present in the spleen and thymus, whereas αA crystallin is expressed not only in the eye lens, but also in several other tissues such as the heart, skeletal muscle, placenta, lung, and kidney.

The main function of these proteins in the lens appears to provide transparency and prevent precipitation by binding to other aggregation-prone proteins. In the lens, αA and αB crystallins exist as heteroaggregates of approximately 800 kDa. Both the recombinant αA and αB crystallins exist as high molecular mass oligomeric proteins of approximately 640 and 620 kDa, respectively. The size of these proteins can vary a little depending on the pH and ionic strength, and they differ in structure, function, tissue expression, and abnormal deposition in disease.

αB crystallin has a heat shock element upstream to the gene and is induced during stress. Apart from maintaining lens transparency, its in vivo functions include interaction with intermediate filaments and regulation of cytomorphological rearrangements during development. αB crystallin is hyperexpressed in neurological disorders such as Alzheimer's disease, Creutzfeldt-Jacob disease, and Parkinson's disease.

The charge C-terminal domain is conserved in all the members of the small heat shock protein family, whereas the hydrophobic N-terminal domain is variable in length and sequence similarity. The N- and C-terminal domains are thought to form two structural domains with an exposed C-terminal extension.

To investigate the role of the N-terminal domains in the differential structural and functional properties of human αA and αB crystallins, the inventors herein swapped their N-terminal domains coded by exon 1. A unique XmnI restriction site at the beginning of the α-crystallin domain in a 20-nucleotide stretch in exon 2, with 100% sequence identity human αA and αB crystallin genes, has been used to create chimeric proteins αANBC and αBNAC. The inventors herein used biophysical methods to study the structural and functional properties of wild-type αA and αB crystallins as well as the chimeras in order to get an insight into the effect of swapping and the role of N-terminal domain in oligomerization and chaperone-like activity.

OBJECT OF THE PRESENT INVENTION

The main object of the present invention is to develop a chimera using αA and αB crystallins.

Another main object of the present invention is to develop a chimeric protein α BNAC crystallin having extraordinarily high chaperone-like activity.

Yet another object of the present invention is to develop a method of preventing protein aggregation using chimeric protein α BNAC crystallin.

Still another object of the present invention is to develop a protein capable of preventing aggregation of overexpressed proteins.

Still another object of the present invention is to develop a method of over expressing chimera α BNAC crystallin.

Still another object of the present invention is to develop a method of over expressing chimera α BNAC crystallin.

SUMMARY OF THE PRESENT INVENTION

The present invention relates to a chimera α BNAC of SEQ ID NO:1 and to a corresponding chimeric protein α BNAC crystallin of SEQ ID NO:2, with the chimeric protein having extraordinarily high chaperone-like activity. The present invention also relates to a method of preventing protein aggregation using the described protein.

DETAILED DESCRIPTION OF THE PRESENT INVENTION

Accordingly, the present invention relate to a chimera α BNAC of SEQ ID NO:1 and to a corresponding chimeric protein α BNAC crystallin of SEQ ID NO:2, with the chimeric protein having extraordinarily high chaperone-like activity. The present invention, in addition, relates to a method of preventing protein aggregation using the described chimeric protein.

BRIEF DESCRIPTION OF THE ACCOMPANYING DRAWINGS

FIG. 1 shows the schematic description of the design of chimeric constructs.

FIG. 2 shows FPLC gel filtration profiles of wild-type αA and αB crystallins and chimeric proteins on a Superose-6 column. A, wild-type αA crystallin (—) and wild-type crystallin αB (-). B, αANBC chimera (—) and αBNAC chimera (-). The void volume (a) and elution positions of thyroglobulin (669 kDa) (b), ferritin (440 kDa) (c) and catalase (232 kDa) (d) are also indicated.

Figure 5:
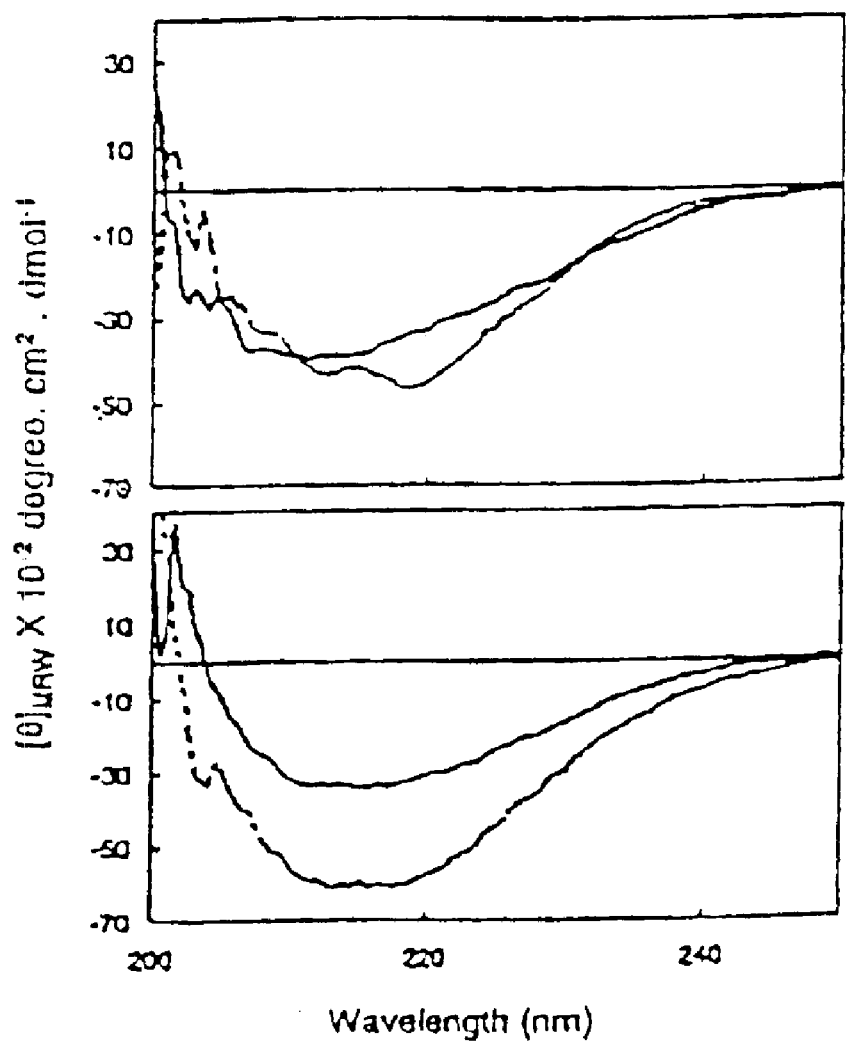

FIG. 5 shows the Far-UV CD spectra of wild-type αBNAC αA and αB crystallins and chimeric proteins. A, wild-type αA crystallin (-) and wild-type αB crystallin (—). B, αANBC (—) and αBNAC (-). The samples were prepared in 50 mM Tris-HCl buffer, pH 7.4, containing 100 mM NaCl and 1 mM EDTA.

Figure 6:
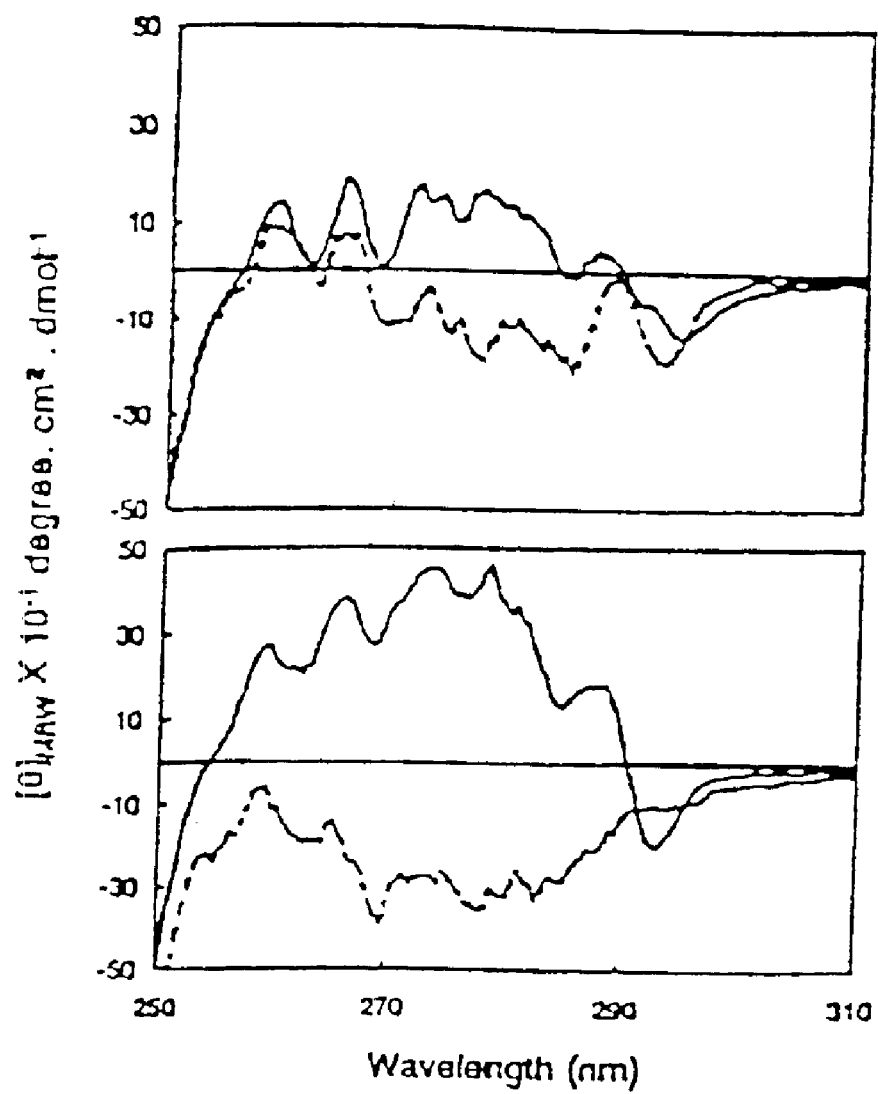

FIG. 6 shows Near-UV CD spectra of wild-type αA and αB crystallins and chimeric proteins. A, wild-type αA crystallin (-) and wild-type αB crystallin (—). B, αANBC (—) and αBNAC (-). The samples were prepared in 50 mM Tris-HCl buffer, pH 7.4, containing 100 mM NaCl and 1 mM EDTA.

Figure 7:
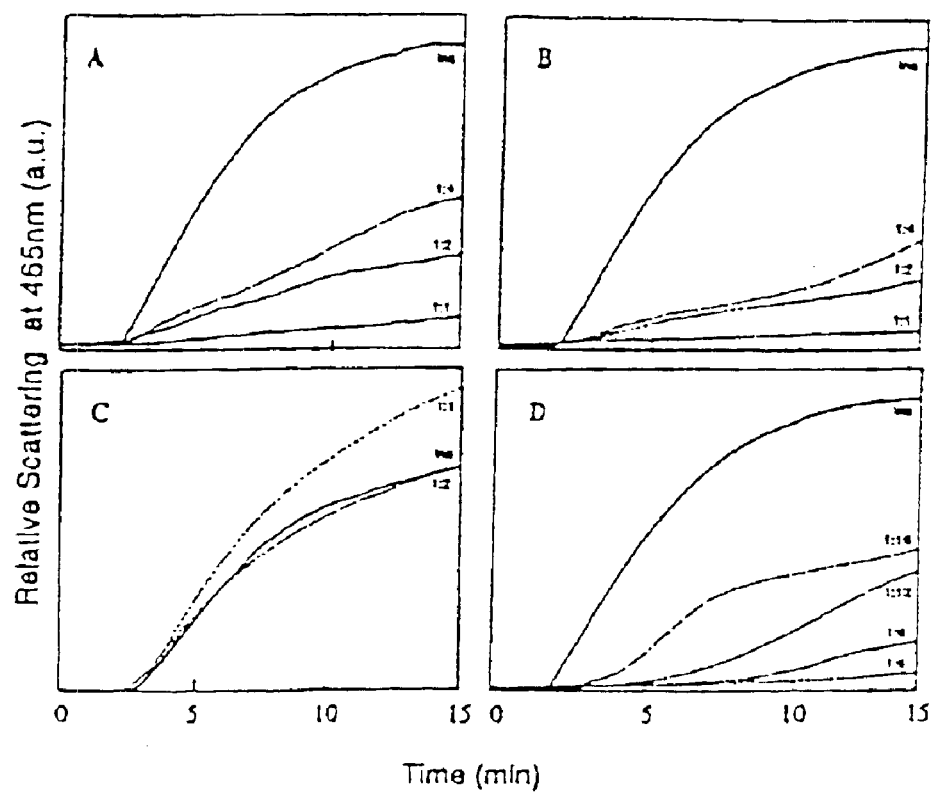

FIG. 7 shows Chaperone-like activity of wild-type αA and αB crystallins and chimeric proteins. A, effect of wild-type αA crystallin. DTT-induced aggregation of 0.2 mg/ml insulin alone (Ins) and in the presence of 1:1, 1:2, and 1:4 w/w wild-type αA crystallin:insulin, respectively. B, effect of wild-type αB crystallin. The panel shows aggregation of 0.2 mg/ml insulin along (Ins) and in the presence of 1:1, 1:2, and 1:4 w/w wild-type αB crystallin:insulin, respectively. C, effect of αANBC chimera. The panel shows aggregation of 0.2 mg/ml insulin along (Ins) and in the presence of 1:2 and 1:1 w/w αANBC:insulin, respectively. D, effect of αBNAC chimera. The panel shows aggregation of 0.2 mg/ml insulin alone (Ins) and in the presence of 1:6, 1:8, 1:12, and 1:16 w/w αBNAC :insulin, respectively.

Figure 8:
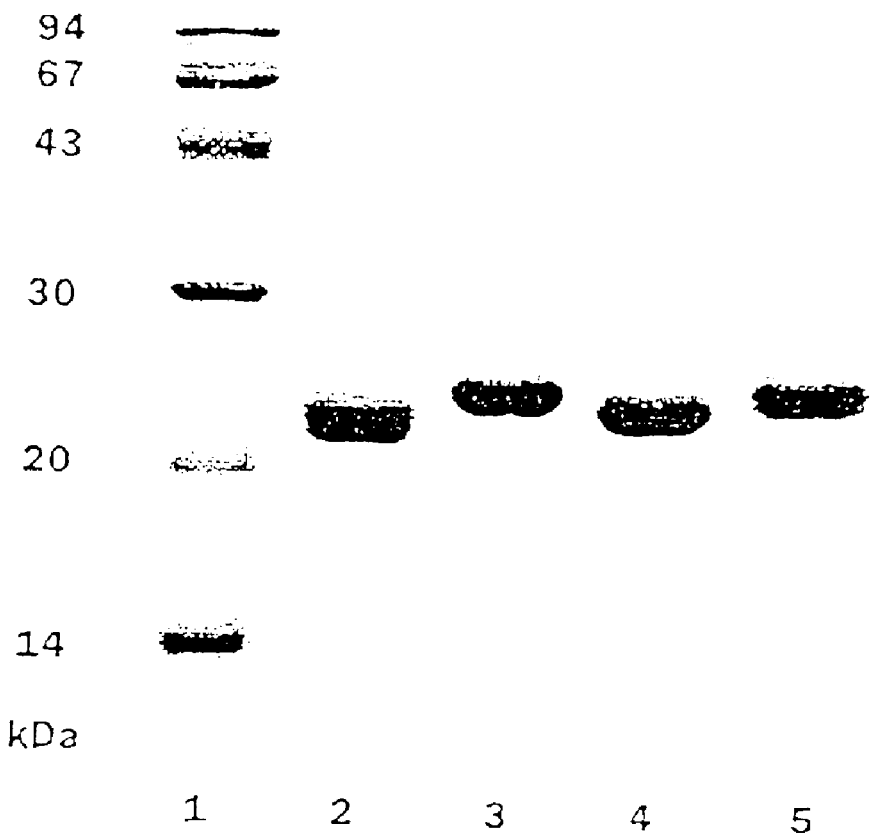

FIG. 8 shows purified human recombinant wild-type and chimeric proteins. 1) Low Molecular mass marker 2) αA wild-type, 3) αB wild-type 4) αANBC and 5) αBNAC.

FIG. 9 is the AlphaBNAC: DNA Sequence NO:1.

FIG. 10 is the Protein Sequence: (DNA Sequence NO: 2).

DETAILED DESCRIPTION OF THE PRESENT INVENTION

Accordingly, the present invention relate to a chimera αBNAC of SEQ ID No: 1 and to a corresponding chimeric protein αBNAC crystallin of SEQ ID NO: 2 with the chimeric protein having extraordinarily high chaperone-like activity. The present invention, in addition, relates to a method of preventing protein aggregation using the described chimeric protein.

One embodiment of the present invention relates to a chimera α BNAC of SEQ ID NO:1. (FIG. 9)

In another embodiment of the present invention, the described chimera is consists of eye lens crystallin α A with exon 1 of the same being replaced with exon 1 of eye lens crystallin α B.

In yet another embodiment of the present invention, the described chimera is an oligonucleotide having a total of 531 nucleotides.

In a further embodiment of the present invention, a chimeric protein α BNAC of SEQ ID NO:2 (FIG. 10) corresponds to the above-mentioned chimera with a length of 531 nucleotides.

In another embodiment of the present invention, the chimeric protein consists of a total of 177 amino acids.

In yet another embodiment of the present invention, the net charge of each unit of the chimeric protein is −5.

In still another embodiment of the present invention, the chimeric protein forms a beta-sheet structure.

In still another embodiment of the present invention, the N-terminal domain of the chimeric protein contains nine proline residues.

In still another embodiment of the present invention, the chimeric protein shows an increase in accessible hydrophobic regions as compared to eye lens crystallins α A and α B.

In still another embodiment of the present invention, the chimeric protein forms larger size oligomers as compared to eye lens crystallins α A and α B.

In still another embodiment of the present invention, the chimeric protein shows an increase in intersubunit interaction as compared to the eye lens crystallins α A and α B.

In still another embodiment of the present invention, wherein said chimeric protein forms larger aggregates as compared to said eye lens crystallins α A and α B.

In still another embodiment of the present invention, amino acid residues of tryptophan in the chimeric protein are less solvent accessible as compared to those of eye lens crystallins α A and α B.

In still another embodiment of the present invention, the chimeric protein forms larger porous oligomers as compared to eye lens crystallins α A and α B.

In still another embodiment of the present invention, the chimeric protein shows increased ellipticity as compared to eye lens crystallins α A and α B.

In a further embodiment of the present invention, a method is disclosed for producing chimera α BNAC crystallin of SEQ ID NO:1 and a chimeric protein α BNAC crystallin thereof having extraordinarily high chaperone-like activity.

In another embodiment of the present invention, the excising of exon 1 of α A crystallin coding for N-terminal domain of eye lens protein α A crystallin using restriction enzyme XmnI is disclosed.

In yet another embodiment of the present invention, the excising of exon 1 of α B crystallin coding for N-terminal domain of eye lens protein α B crystallin using restriction enzyme XmnI is disclosed.

In still another embodiment of the present invention, substitution of the excised exon 1 of α A crystallin with excised exon 1 of α B crystallin in α A crystallin is disclosed.

In still another embodiment of the present invention, the obtaining of chimera α BNAC crystallin is disclosed.

In still another embodiment of the present invention, the expressing of the α BNAC crystallin in *E. Coli is disclosed.*

In still another embodiment of the present invention, the purifying of an expressed chimeric protein α BNAC crystallin is disclosed.

In still another embodiment of the present invention, the restriction enzyme XmnI cleaves α A and α B crystallins at a site having a sequence homology of 20 nucleotides.

In still another embodiment of the present invention, the reading frame of the chimera α BNAC crystallin is the same as that of the eye lens crystallins α A and α B.

In still another embodiment of the present invention, the purified chimeric protein shows more than 95% purity.

In a further embodiment of the present invention, a method of using chimeric protein α BNAC crystallin of SEQ ID 2 for preventing protein aggregation is disclosed:

In another embodiment of the present invention, the step of mixing test protein with the chimeric protein is disclosed.

In still another embodiment of the present invention, the step of incubating the mixture at room temperature is disclosed.

In still another embodiment of the present invention, the step of adding a protein denaturing agent to the mixture is disclosed.

In still another embodiment of the present invention, the step of estimating protein aggregation (if any) using conventional methods is disclosed.

In still another embodiment of the present invention, the chimeric protein shows extraordinarily high chaperone-like activity ranging between 3 and 6 times as compared to eye lens crystallins α A and α B.

In still another embodiment of the present invention, the test protein is selected from a group comprising fibrous proteins, globular proteins, enzymes, hormones, and structural proteins.

In still another embodiment of the present invention, the concentration of test protein ranges between 0.5 and 5.0 mg/ml.

In still another embodiment of the present invention, the chimeric protein shows enhanced chaperone-like activity with said chimeric protein and test protein in a ratio ranging between 1:1 and 1:25 (w/w).

In still another embodiment of the present invention, the protein denaturing agent is selected from a group comprising acids, alkalis, detergents, organic solvents, and heavy metal cations.

In still another embodiment of the present invention, the protein denaturing agent is preferably dithiothreitol (DTT).

In still another embodiment of the present invention, the amount of 1M of said DTT used is ranges between 5 and 50 µl.

In still another embodiment of the present invention, wherein time duration for incubation is ranging between 5 to 15 minutes.

In still another embodiment of the present invention, protein aggregation is estimated by using spectrophotometry.

In still another embodiment of the present invention, the method of using the chimeric protein helps prevent aggregation of proteins.

In still another embodiment of the present invention, the method of using the chimeric protein helps increase the shelf life of proteins of pharmaceutical value.

Construction of human chimeric αA and αB crystallins for αANBC chimera—The 235-base pair NdeI-XmnI fragment of pCR2.1-αA plasmid was ligated to the 384-base pair XmnI-HindIII fragment of pCR2.1-αB plasmid to generate a chimeric coding region of αANBC. The αANBC chimera with NdeI-HindIII overhangs was then ligated to NdeI-HindIII-linearized expression vector pET21a (Novagen) to produce pET21a-αANBC.

Construction relating to αBNAC chimera—The 247-base pair NdeI-XmnI fragment pCR2.1-αB was ligated to the 446-base pair XmnI-HindIII fragment pCR2.1-αA to generate the chimeric coding region of αBNAC. The αBNAC chimera with NdeI-HindIII overhangs was ligated pET21a to produce pET21a-αBNAC.

Sequencing of human chimeric αANBC and αBNAC crystallins--Sequencing was done with a T7 promoter primer using the dye terminator cycle sequencing kit (Perkin-Elmer) in a 3700 ABI automated DNA sequencer. The coding regions of both the αANBC and αBNAC chimeras were found to be mutationless with no change in the reading frame.

Overexpression and purification of human wild-type and chimeric αA and αB crystallins—The expression plasmids (pET21a-αAwt, pET21a-αBwt, pET21a-αANBC, and pET21a-αBNAC) were transformed into competent Escherichia coli BL21(DE3) cells. Growth, induction, lysis of cells, and purification of chimeric proteins was done as described for recombinant wild-type αA and αB crystallins.

FPLC gel permeation chromatography—Multimeric sizes of the wild-type and chimeric proteins were evaluated on a Superose-6 HR 10/30 prepacked column (dimensions: 10×300 mm, bed volume: 24 ml) with reference to high molecular mass standards (Sigma). Standards used were thyroglobulin (669 kDa), ferritin (440 kDa), and catalase (232 kDa).

Fluorescence measurements—intrinsic fluorescence—Intrinsic fluorescence spectra of wild-type and chimeric proteins were recorded using a Hitachi F-4000 fluorescence spectrophotometer with an excitation wavelength of 295 nm. The excitation and emission band passes were set at 5 and 3 nm, respectively. Intrinsic fluorescence spectra were recorded using 0.2 mg/ml protein in 10 mM phosphate buffer, which was incubated at 37° C. for 10 min.

8-anilino-1-naphthalenesulfonic acid (ANS) binding—Wild-type and chimeric proteins (0.2 mg/ml) in 10 mM phosphate buffer, pH 7.4, containing 100 mM NaCl were equilibrated at 37° C. in the sample holder of a Hitachi F-4000 fluorescence spectrophotometer using a Julabo thermostated water bath for 10 min. To these protein samples, 20 µl of 10 mM ANS was added. Fluorescence spectra were recorded with an excitation wavelength of 365 nm. The excitation and emission band passes were 5 and 3 nm, respectively.

Circular dichroism studies—Circular dichroism spectra were recorded using a Jasco J-715 spectropolarimeter. All spectra reported an average of 5 accumulations. Far- and near-UV CD spectra were recorded using 0.05- and 1-cm pathlength cuvettes, respectively.

Assay for protein aggregation—Chaperone-like activity of the wild-type and chimeric proteins was studied by the insulin aggregation assay. The extent of protection by the wild-type αA and αB crystallins and the chimeric proteins was studied by incubating insulin (0.2 mg/ml) with various concentrations of the wild-type and chimeric proteins for 10 min at 37° C. Aggregation was initiated by the addition of 20 µl of 1 M dithiothreitol (DTT) after the incubation.

Figure 1:
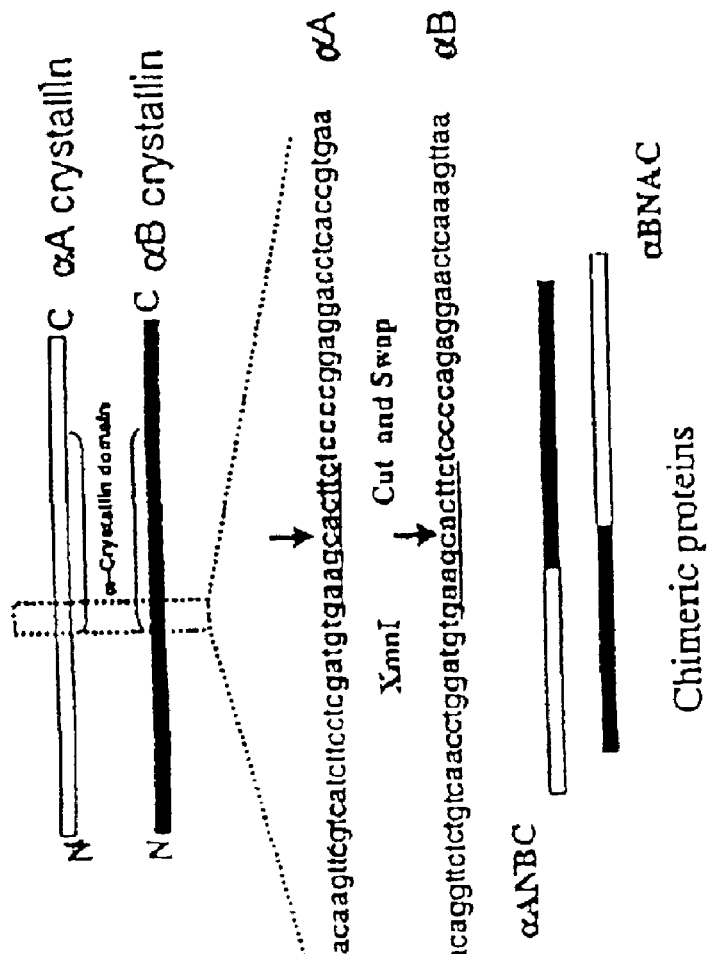

Construction and expression of the chimeric human αA and αB crystallins—Human αA and αB crystallin genes have a unique site for the restriction enzyme XmnI at the beginning of exon 2. A 20 nucleotide stretch at the XmnI site in both αA and αB crystallins has 100% sequence identity. Swapping of the domains does not disturb the reading frame (FIG. 1). Since the XmnI site is slightly into the exon II, the excised N-terminal fragment has an additional 15 amino acids.

Of the 15 amino acids, 8 are identical and the rest are chemically conserved. Ligation of the N-terminal domain of αA crystallin with the C-terminal region of αB crystallin results in the chimeric polypeptide αANBC crystallin, which is 171 amino acids long. Similarly, the ligation of the N-terminal region of αB crystallin with the C-terminal domain of αA crystallin creates a polypeptide αBNAC crystallin that is 177 amino acids long. Henceforth, the chimeras are referred to as αANBC and αBNAC.

Overexpression and purification of the chimeric proteins was carried out as described earlier for the wild-type proteins. The wild-type and chimeric proteins were purified to greater than 95% homogeneity, as judged by SDS-polyacrylamide gel electrophoresis and moved as 20-kDa proteins as expected.

Discontinuance buffer SDS-PAGE analysis (FIG. 8) was performed on 12% gel according to a standard protocol. The sample and stacking gel contained Tris-HCl buffer (pH 6.8), the upper and lower buffer reservoirs contained Tris-Glycine (pH 8.3), and the reservoir gel contained Tris-HCl (pH 8.8). All components of the system contain 0.1% SDS. Samples were prepared in loading buffer (50 mM Tris-HCl pH 6.8 containing 5% beta-mercaptoethanol, 2% SDS, 0.1% bromophenol blue and 10% glycerol), boiled in a water bath for 2–3 minutes and loaded onto the gel. The samples were electrophoresed at a constant current of 20 mA. When the samples entered the resolving gel the current was increased to 30 mA and the run continued till the dye front reached the bottom of the gel. The electrophoresis was stopped and the gel was removed from the plates and strained using coomassie Brilliant Blue R-250.

Interestingly, when αANBC is eluted from a Mono Q ion exchange column with a 0–2 M NaCl gradient, it elutes at 100 mM NaCl like the wild-type αB crystallin. On the other hand, αBNAC elutes at 350 mM NaCl, similar to wild-type αA crystallin.

The number of positively charged residues per monomer of αBNAC crystallin are 20 (Arg+Lys) while the number of negatively charged residues are 25 (Glu+Asp). Thus each subunit of αBNAC has a net negative charge of –5. The N-terminal region of the protein is hydrophobic and is buried in the oligomer. The C-terminal domain may largely determine the surface charge distribution and the solubility of αBNAC.

A recently proposed model for α-crystallin suggests that the hydrophobic N-terminal domain is mostly buried in the oligomer. Thus, the C-terminal domain may largely determine the surface charge distribution of the proteins. This could be one of the reasons for the similarity in Mono Q elution profiles of wild-type proteins and chimeras that contain C-terminal regions identical to those of the wild-type proteins.

Figure 2:
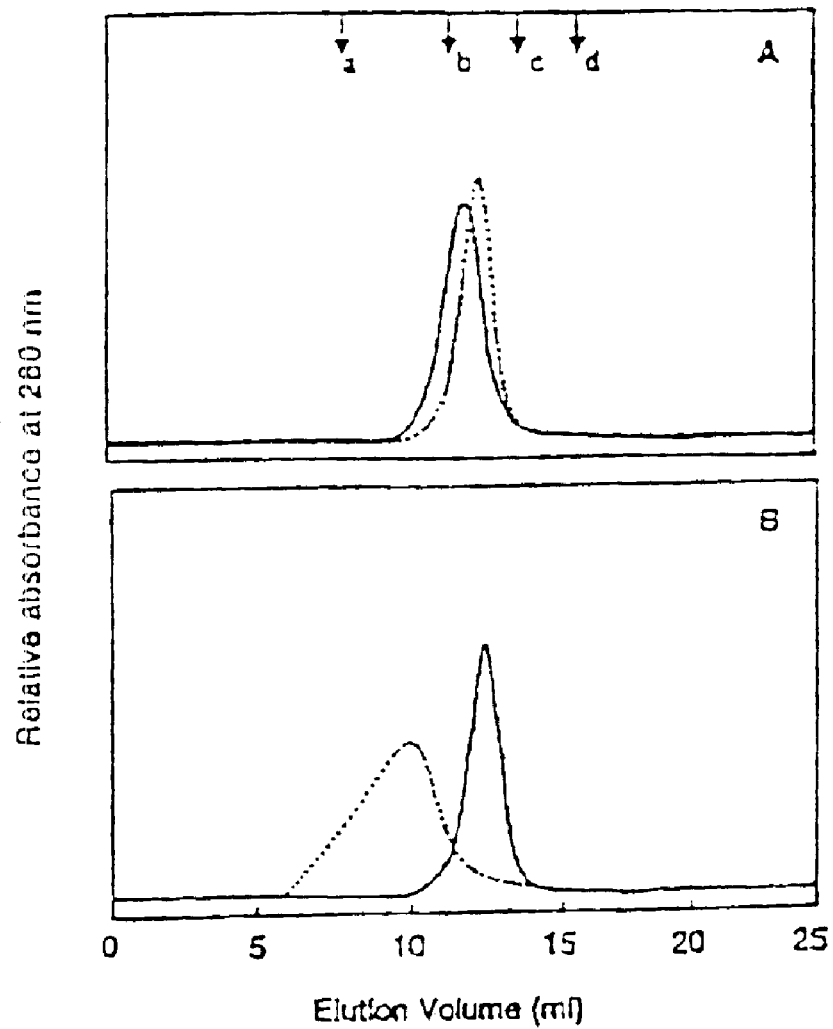

Superpose-6 gel permeation chromatography—To investigate the consequences of domain swapping on the molecular masses, chimeric and wild-type proteins were chromatographed on a FPLC Superose-6 gel filtration column (FIG. 2). The average molecular masses of wild-type αA and αB crystallins were observed to be 640 and 620 kDa, respectively. These sizes are consistent with earlier reports. The chimera αANBC elutes at the same elution volume as that of wild-type αB with an apparent molecular mass of 620 kDa. However, the αBNAC chimera oligomerizes into large polydisperse aggregates, with species exceeding 2000 kDa. This finding shows an important difference in αA and αB crystallins.

The αANBC chimera consisting of the N-terminal domain of αA crystallin and the C-terminal domain of αB crystallin still possesses the, oligomer size of wild-type αA and αB crystallins. Thus, it appears that the N-terminal domain of αB crystallin can be replaced by the N-terminal domain of αA crystallin with no alteration in the oligomeric status. However, the N-terminal domain of αB crystallin in fusion with the C-terminal domain of αA crystallin forms very large aggregates, probably due to altered packing of the subunits with an increase in intersubunit unit interaction. This kind of increase in the oligomer size was earlier observed in the R116C mutant of αA crystallin (15). The monomer sizes of the proteins of the small heat shock protein family range from 12 to 43 kDa. Almost all members of this family multimerize to form large aggregates, ranging in size from 400 to 800 kDa with only one exception till date, in the form of sHSP 12.6 of Caenorhabditis elegans, which has the shortest N- and C-terminal domains, and is monomeric.

The N-terminal domain is variable in both length and sequence in the sHSP super-family, which might be responsible for the varying multimeric sizes. Bova et al. showed that sequential truncation from the N terminus of αA crystallin reduces oligomeric size. In the present study, the sequence length of the swapped N-terminal domain between αA and αB crystallin is similar, so the variation in sequence of this domain is likely to be responsible for the differential multimerization of the chimeric proteins.

Figure 3:
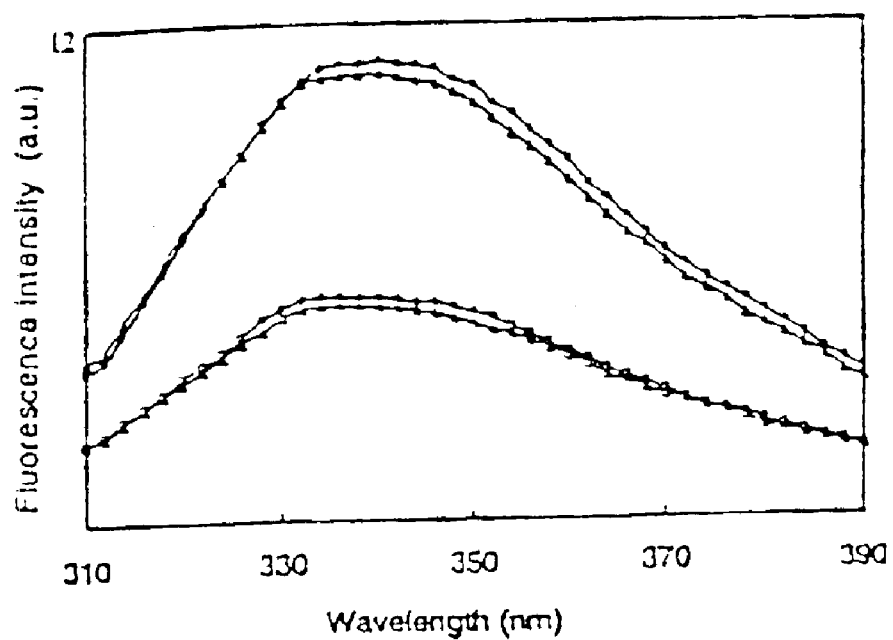
FIG. 3 shows the intrinsic fluorescence spectra of wild-type αA crystallin (O), wild-type αB crystallin (•), αANBC (Δ), and αBNAC (▲)

Intrinsic and ANS fluorescence—The emission maximum of tryptophan is highly sensitive to solvent polarity and depends on the accessibility of tryptophan residues to the aqueous phase. FIG. 3 shows the intrinsic fluorescence spectra of wild-type and chimeric proteins. The intrinsic fluorescence spectra of the wild-type αB crystallin and αBNAC are similar. Both the tryptophans are present in the N-terminal domain, which are likely to be in a similar environment even after domain swapping. A slight blue shift, noticeable in the red region of the emission profile of αBNAC compared with the wild-type αB crystallin, suggests that the tryptophans in the chimera are marginally less solvent-accessible.

Figure 4:
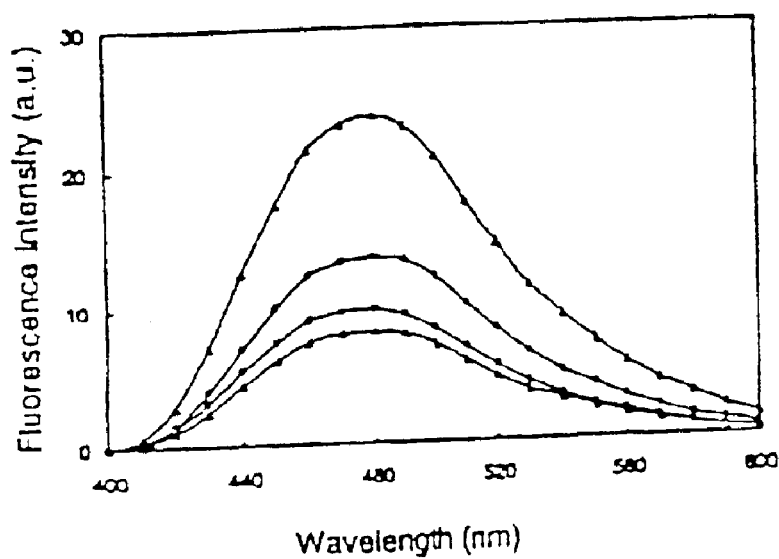
FIG. 4 is the normalized fluorescence emission spectrum of ANS bound to wild-type αA crystallin (O), wild-type αB crystallin (•), αANBC (Δ), and αBNAC (▲).

The intrinsic fluorescence spectra of the lone tryptophan of wild-type αA crystallin, which is present in the N-terminal domain, and αANBC are similar, indicating no alteration of the tryptophan environment in the chimeric αANBC protein with respect to the wild-type αA crystallin. FIG. 4 shows the spectra of ANS in the presence of wild-type and chimeric proteins. ANS fluorescence spectra show marked differences in emission intensity with no apparent change in emission maxima. The αANBC chimera binds the least amount of ANS among all the proteins compared. The αBNAC chimera, on the other hand, binds ANS several times more when compared with wild-type αB crystallin, wild-type, αA. crystallin, and αANBC chimera.

This finding proves that there are more hydrophobic regions accessible to ANS in the αBNAC chimera than in αANBC chimera. However, the gel permeation chromatography data together with ANS fluorescence suggest that αBNAC might be forming a large porous oligomer.

Circular dichroism measurements of chimeric αANBC and αBNAC crystallins—FIG. 5 shows far-UV circular dichroism spectra of wild-type and chimeric proteins. CD spectra of wild-type αA and αB crystallins, shown in panel A, are comparable with the CD spectra of recombinant human αA and αB crystallins reported earlier. Both the spectra show characteristic β-sheet protein profile as expected. Chimeric proteins also show j3-sheet CD profiles. The CD spectrum of αANBC is comparable to the spectra of wild-type αA and αB crystallins. However, αBNAC shows increased ellipticity.

Near-UV CD spectra (FIG. 6) also show a similar trend. Spectra of wild-type αA and αB are comparable to earlier reported spectra for recombinant human αA and αB crystallins. The CD spectrum of the chimeric αANBC is comparable to that of αB crystallin with increased chirality for αANBC. The CD spectrum of αBNAC on the other hand is comparable to that of wild-type αA crystallin.

It was found that domain swapping results in some change in secondary and tertiary structure of αANBC with observable change only in the secondary structure for αBNAC.

Chaperone-like activity—Insulin B-chain aggregates in the presence of DTT. At 37° C. a 1:1 (w/w) ratio of wild-type αA and αB crystallin to insulin prevented this aggregation completely. At ratios of 1:2 and 1:4, aggregation was prevented to lesser extents, as shown in FIG. 7 (panels A and B). Interestingly, the chimera αBNAC showed enhanced chaperone-like activity. The initial scatter value for αBNAC chimera without insulin was very high. The large molecular size of αBNAC could be responsible for the high scatter. A similar high initial scatter value for the R116C mutant of αA crystallin, which also forms a large aggregate (>2000 kDa) was observed earlier by the inventors. The data were normalized to determine the protective ability of the ≠BNAC protein. At 37° C. complete protection was observed at a 1:6 w/w ratio of αBNAC to insulin. Significant protection was observed even at 1:8, 1:12, and 1:16 ratios of αBNAC to insulin (FIG. 7D).

The αBNAC chimera shows 3–to 4-fold increase in the chaperone-like activity compared with the wild-type proteins. αANBC, in contrast, shows complete loss of chaperone-like activity. A 1:2 (w/w) ratio of αANBC to insulin does not show any protective ability toward DTT-induced aggregation of insulin. Increasing the αANBC ratios to 1:1 and 2:1 w/w with respect to insulin does not show any increase in protection (FIG. 7C). In fact, αANBC promotes the aggregation process as observed by increased light scattering.

The swapped N-terminal domain (exon 1 encoded) is comparable in length between human αA and αB crystallins. There are some differences in the sequences in this region. One of the prominent differences is the increase in the number of proline residues. The N-terminal domain of αA crystallin contains 5 proline residues, whereas the same region for αB crystallin has 9 proline residues (two prolines in tandem).

The swapping alters the number of proline residues in the chimeric proteins. αBNAC contains 9 prolines in its N-terminal domain, a gain of 4 prolines in comparison to the same region of wild-type αA crystallin. Far-UV CD spectrum shows some enhancement in the secondary structure. Whether the local secondary structural changes can alter the subunit topology and consequently intersubunit interactions remains to be investigated. Although differences in the number of proline residues have been pointed out, there are other sequence variations, and marginal changes in predicted pI and the total length of the chimeric proteins. Clearly discernible changes are oligomeric status, accessible hydrophobic surfaces, and chaperone-like activity.

It is interesting to note that, despite being similar to wild-type αB crystallin in the aggregate molecular mass and circular dichroism spectra, the chimeric αANBC possesses no chaperone-like activity. The most important difference between the two chimeric proteins is the accessible hydrophobicity. ANS, a hydrophobicity probe, very clearly distinguishes the two chimeric proteins. The lack of accessible surface hydrophobicity is due to altered subunit packing in αANBC chimera, which results in its loss of chaperone-like activity.

The enhanced chaperone-like activity of αBNAC chimera is because of the exposure and availability of more hydrophobic surfaces when compared with the wild-type proteins. Increased ANS binding of the αBNAC chimera supports this conclusion.

The inventors observed an increase in oligomeric size and chaperone-like activity in the case of the αBNAC chimera. However, the increase in size and enhancement of chaperone-like activity need not necessarily be correlated. The point mutation R116C in αA crystallin leads to increased oligomer size but results in significant loss of chaperone-like activity.

Swapping the N-terminal domain between human αA and αB crystallins makes a more effective chaperone in the case of αBNAC chimera, whereas αANBC chimera loses its protective abilities completely. To the best of the inventors' knowledge, this is the first report where a 3–4-fold increase in chaperone-like activity has been observed. This phenomenon may has a therapeutic significance in diseases occurring due to protein misfolding.

What is claimed is:

1. A chimeric protein αBNAC, of SEQ ID NO:2.

2. A chimeric protein as claimed in claim 1, wherein said chimeric protein is consists of a total of 177 amino acids.

3. A chimeric protein as claimed in claim 1, wherein the net charge of each unit of said chimeric protein is −5.

4. A chimeric protein as claimed in claim 1, wherein said chimeric protein forms beta-sheet structure.

5. A chimeric protein as claimed in claim 1, wherein the N-terminal domain of said chimeric protein contains nine proline residues.

6. A chimeric protein as claimed in claim 1, wherein said chimeric protein shows an increase in accessible hydrophobic regions as compared to eye lens crystallins αA and αB.

7. A chimeric protein as claimed in claim 1, wherein said chimeric protein forms larger size oligomers as compared to eye lens crystallins αA and αB.

8. A chimeric protein as claimed in claim 1, wherein said chimeric protein shows an increase in intersubunit interaction as compared to eye lens crystallins αA and αB.

9. A chimeric protein as claimed in claim 1, wherein said chimeric protein forms larger aggregates as compared to eye lens crystallins αA and αB.

10. A chimeric protein as claimed in claim 1, wherein amino acid residues of tryptophan in said chimeric protein are less solvent accessible as compared to those of eye lens crystallins αA and αB.

11. A chimeric protein as claimed in claim 1, wherein said chimeric protein forms larger porous oligomers as compared to eye lens crystallins αA and αB.

12. A chimeric protein as claimed in claim 1, wherein said chimeric protein shows increased ellipticity as compared to eye lens crystallins αA and αB.

* * * * *

SEQUENCE LISTING

<160> NUMBER OF SEQ ID NOS: 2

<210> SEQ ID NO 1
<211> LENGTH: 531
<212> TYPE: DNA
<213> ORGANISM: Artificial Sequence
<220> FEATURE:
<223> OTHER INFORMATION: DNA sequence for chimeric alpha BNAC

<400> SEQUENCE: 1

```
atggacatcg ccatccacca ccctggatc cgccgccct tctttccttt ccactccccc      60
agccgcctct tgaccagtt cttcggagag cacctgttgg agtctgatct tttcccgacg     120
tctacttccc tgagtccctt ctaccttcgg ccaccctcct tcctgcgggc acccagctgg    180
tttgacactg gactctcaga gatgcgcctg gagaaggaca ggttctctgt caacctggat    240
```

```
gtgaagcact tctccccgga ggacctcacc gtgaaggtgc aggacgactt tgtggagatc    300
cacggaaagc acaacgagcg ccaggacgac cacggctaca tttcccgtga gttccaccgc    360
cgctaccgcc tgccgtccaa cgtggaccag tcggccctct cttgctccct gtctgccgat    420
ggcatgctga ccttctgtgg ccccaagatc cagactggcc tggatgccac ccacgccgag    480
cgagccatcc ccgtgtcgcg ggaggagaag cccacctcgg ctccctcgtc c             531
```

<210> SEQ ID NO 2
<211> LENGTH: 177
<212> TYPE: PRT
<213> ORGANISM: Artificial Sequence
<220> FEATURE:
<223> OTHER INFORMATION: Sequence of chimeric protein alpha BNAC

<400> SEQUENCE: 2

```
Met Asp Ile Ala Ile His His Pro Trp Ile Arg Arg Pro Phe Phe Pro
1               5                  10                  15

Phe His Ser Pro Ser Arg Leu Phe Asp Gln Phe Phe Gly Glu His Leu
            20                  25                  30

Leu Glu Ser Asp Leu Phe Pro Thr Ser Thr Ser Leu Ser Pro Phe Tyr
        35                  40                  45

Leu Arg Pro Pro Ser Phe Leu Arg Ala Pro Ser Trp Phe Asp Thr Gly
    50                  55                  60

Leu Ser Glu Met Arg Leu Glu Lys Asp Arg Phe Ser Val Asn Leu Asp
65                  70                  75                  80

Val Lys His Phe Ser Pro Glu Asp Leu Thr Val Lys Val Gln Asp Asp
                85                  90                  95

Phe Val Glu Ile His Gly Lys His Asn Glu Arg Gln Asp Asp His Gly
            100                 105                 110

Tyr Ile Ser Arg Glu Phe His Arg Arg Tyr Arg Leu Pro Ser Asn Val
        115                 120                 125

Asp Gln Ser Ala Leu Ser Cys Ser Leu Ser Ala Asp Gly Met Leu Thr
    130                 135                 140

Phe Cys Gly Pro Lys Ile Gln Thr Gly Leu Asp Ala Thr His Ala Glu
145                 150                 155                 160

Arg Ala Ile Pro Val Ser Glu Arg Glu Lys Pro Thr Ser Ala Pro Ser
                165                 170                 175

Ser
```